United States Patent [19]

Jensen

[11] Patent Number: 5,449,817
[45] Date of Patent: Sep. 12, 1995

[54] PROCESS FOR THE PREPARATION OF ORGANIC ISOCYANATES

[75] Inventor: Arne T. Jensen, Hillerød, Denmark
[73] Assignee: Haldor Topsoe A/S, Denmark
[21] Appl. No.: 191,630
[22] Filed: Feb. 4, 1994

[30] Foreign Application Priority Data

Feb. 12, 1993 [DK] Denmark .................. 0160/93

[51] Int. Cl.⁶ .................................. C07C 263/04
[52] U.S. Cl. ............................................. 560/345
[58] Field of Search .................................. 560/345

[56] References Cited

U.S. PATENT DOCUMENTS

| | | | |
|---|---|---|---|
| 3,668,250 | 6/1972 | Karafian | 260/555 |
| 4,341,640 | 7/1982 | Landis | 210/752 |

OTHER PUBLICATIONS

Chemical Abstracts, Fukuoka, 104: 207855, Nov. 25, 1985.
Patent Abstracts of Japan, vol. 19, No. 107 (C-341) 1986 & JP-A-60 237 058 (Asahi Kasei Kogyo KK) Abstract.
Patent Abstracts of Japan, vol. 17, No. 37 (C-1019) 25 Jan. 1993 & JP-A-04 253 951 (Asahi Chem Ind Co. Ltd.) Abstract.

Primary Examiner—Jose G. Dees
Assistant Examiner—Samuel Barts
Attorney, Agent, or Firm—Ostrolenk, Faber, Gerb & Soffen

[57] ABSTRACT

The preparation of organic isocyanates of formula by the thermal decomposition of the corresponding carbamates in an inert solvent, is improved by thermally treating the dissolved carbamate in separate steps, decomposing the carbamate to isocyanate and alcohol, with intermediate steps of removing the alcohol with an inert stripping agent, recovering a solution rich in isocyanate.

10 Claims, 1 Drawing Sheet

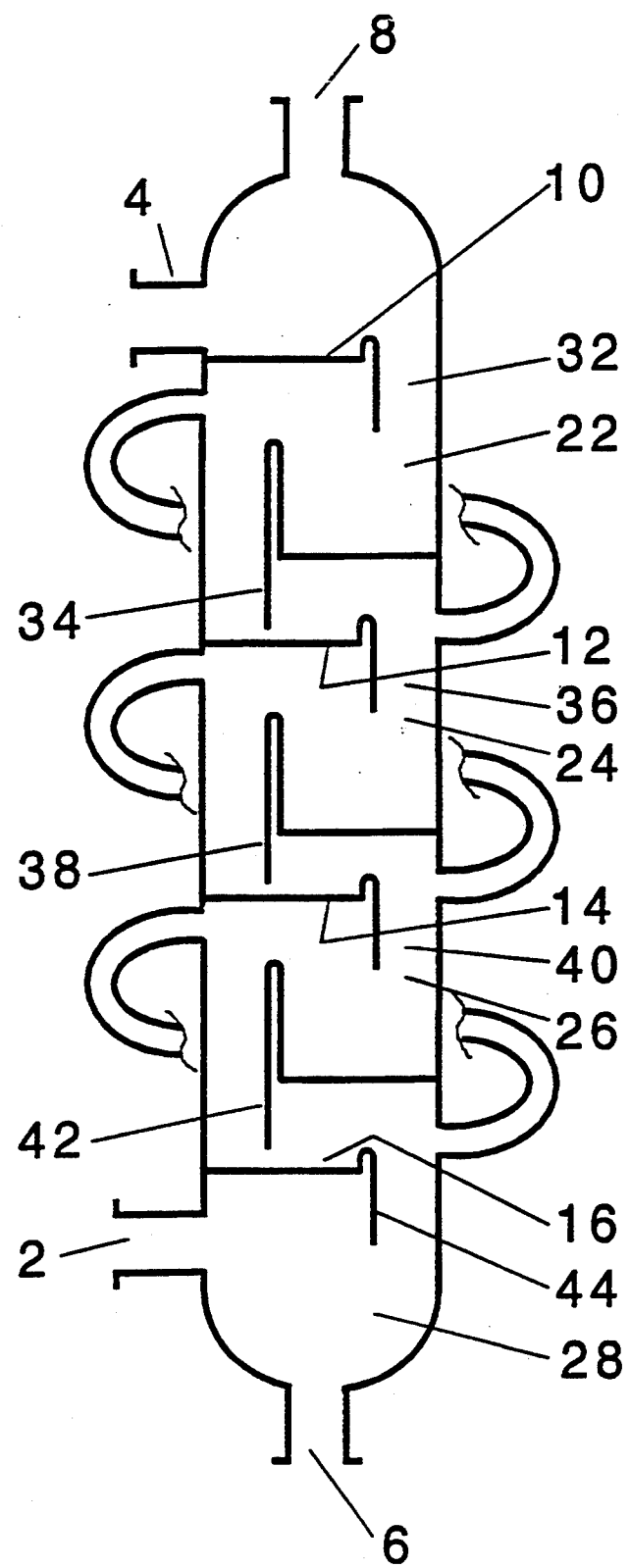

PROCESS FOR THE PREPARATION OF ORGANIC ISOCYANATES

BACKGROUND OF THE INVENTION

The present invention is directed to the preparation of organic isocyanates. In particular, the invention concerns preparation of diphenylmethane diisocyanates and related higher homologs, polymethylene polyphenyl isocyanates, from corresponding carbamates in a multistep thermal decomposition process.

Diphenylmethane diisocyanates and polymethylene polyphenyl isocyanates, generally referred to as "MDI" and "PMPPI", are widely used in the production of polyurethanes.

Industrial processes for manufacture of MDI and PMPPI are conventionally based on reaction of phosgene with methylenedianiline or salts thereof. Due to the volatility and toxicity of phosgene, other methods have recently been developed, which do not require the use of phosgene.

The known non-phosgene processes involve thermal decomposition of carbamates.

Thermal decomposition of carbamates is either carried out in the vapour phase at high temperatures or in the liquid phase at lower temperatures.

Due to the high temperatures necessary in the vapour phase decomposition processes and serious side reactions caused by the high temperature conditions, the liquid phase process has gained increasing interest in the commercial production of isocyanates.

In the liquid phase processes described in the literature, the carbamates are decomposed to the corresponding isocyanate and alcohol typically at temperatures between 170° C. and 350° C., while being dissolved in an inert solvent (GB Patent No. 1,458,595; U.S. Pat. No. 4,292,254).

To obtain the desired product yield, the reaction time is generally between 30 minutes and a few hours. Produced isocyanates and alcohol formed during the thermal decomposition of carbamates are then recovered separately by distillation of the solution and/or stripping with an inert stripping agent.

The decomposition of carbamates is a fairly slow process and catalysts have been proposed to speed up the reaction (EP Patent No. 28,337). Additionally, the equilibrium at conditions employed during thermal decomposition of carbamates is unfavourable for extensive decomposition to the alcohol plus isocyanates in the solvent.

Consequently, to permit high yield of the desired isocyanates the alcohol-to-isocyanate ratio in the liquid phase should be constantly at a minimum.

SUMMARY OF THE INVENTION

Based on the above consideration, the present invention provides a process for the preparation of organic isocyanates having the general formula:

where
Ar is a single or multiple substituted phenylgroup;
R is a methylene or an ethylene group; and
n is a whole number of from 0 to 2, by thermal decomposition of corresponding carbamates in the presence of an inert solvent, the improvement of which comprises thermally treating the carbamate dissolved in the solvent in multiple and separate steps and, thereby, decomposing the carbamate to the isocyanate and an alcohol;

in intermediate steps removing the alcohol formed during the thermal treatment by stripping the solvent between the steps of thermal treatment with an inert stripping agent; and finally
recovering a solution being rich in the isocyanate.

When carrying out thermal decomposition of carbamates stepwise with removal of formed alcohol between the decomposition steps, the solution is in a reaction column successively and alternately under decomposition and stripping treatment resulting in improved decomposition and alcohol removal at a high flow rate of the solution containing the starting carbamate.

Thereby, the equilibrium of the decomposition reaction:

is advantageously shifted towards formation of isocyanate.

Furthermore, the high degree of alcohol removal from the solution between the decomposition steps provides a low alcohol-isocyanate concentration ratio, which by the aforementioned reasons improves product yield. Depending on the specific starting carbamate and solvent used in the process, temperature and pressure conditions will usually be in the range of between 160° C. and 300° C. at about 2-5 bars.

Solvents, which are appropriate with the above process conditions, include aliphatic hydrocarbons having from 8 to 16 carbon atoms and alkylated or halogenated aromatic compounds, preferably decaline, o-diethylbenzene, o-dichlorobenzene, dodecane, hexadecane and biphenyl.

The process as described above is especially useful in the preparation of MDI and PMPPI from the corresponding methyl or ethyl carbamates MDU and PMPPU. During preparation of MDI and PMPPI an attractive solvent is o-dichlorobenzene, which shows good solubility to both the starting materials and the products, including methanol or ethanol generated in the decomposition steps. The o-dichlorobenzene solvent is, furthermore, convenient as stripping agent in the process.

In operating the process according to the invention at the above process conditions, a starting carbamate, e.g. diphenylmethane carbamate (MDU), is dissolved in a suitable solvent, as described above, with a concentration of between 1 and 20% by weight. The actual concentration of the carbamate in the solvent will depend on the purity desired for the final MDI-product. Low carbamate concentrations provide high product purity, because of the high dilution factor of generated MDI, alcohol and unconverted MDU being present in the solvent during decomposition. Decomposition of highly diluted starting materials, demands higher energy consumption in the recovery of MDI product for the evaporation of the solvent in the final process step. More concentrated solutions of the starting material save energy in the final recovery step, but result in somewhat poorer product quality, due to side reaction of the carbamate with the reactive isocyanate in the solvent during the decomposition steps.

Decomposition of the MDU starting solution is carried out after introduction of the solution into a reaction column provided with alternating stripping trays and reaction volumes. In the reaction volumes MDU in the solution is successively decomposed to MDI and alcohol, as described herein before. Subsequent to each decomposition step generated alcohol is stripped off by passing the solution over stripping trays arranged after each reaction volume. Each stripping tray is conventionally designed as fritted disc, sieve tray, or valve tray provided with bubble cups or the like. During passage on the trays, alcohol is removed from the solution into the vapour phase by vapours of an inert stripping agent. As mentioned above, vapourized o-dichlorobenzene solvent from the final recovery of MDI product may advantageously be used as stripping agent. Through action of the stripping agent when bubbling through the solution on the trays, the lower boiling alcohol is substantially removed from the solution after each decomposition step and recovered as head product together with vapours of the stripping agent.

After removal of the alcohol, the solution containing MDU and MDI is subjected to further MDU decomposition by heat treatment in a number of reaction volumes succeeded by alcohol removal on stripping trays located after each reaction volume.

By passage through alternating stripping and decomposition stages the concentration of MDI in the solution is continuously increased and a MDI rich solution leaves finally the column as bottom product.

The desired MDI product may afterwards be recovered from the bottom product by conventional evaporation of the solvent.

BRIEF DESCRIPTION OF THE DRAWING

The sole FIGURE is a schematic representation of the process of the invention carried out in a reaction column.

DETAILED DESCRIPTION OF THE PREFERRED EMBODIMENT

The above aspects and features of the invention will become more evident by the following description with reference to the drawing.

The reaction column comprises within a shell a series of reaction volumes 22, 24, 26, 28 and stripping trays 10, 12, 14, 16 arranged between the reaction volumes. As to the flow of a feedstream through the column, the reaction volumes and the stripping trays are interconnected by drain-plates 32, 34, 36, 38, 40, 42, 44. The reaction column further comprises inlet 4 for introduction of a carbamate containing feed-solution and outlet 6 for withdrawal of an isocyanate rich product-solution.

A stripping agent is passed through an inlet 2 to bottom stripping tray 16. The stripping agent is further distributed to stripping trays 14, 12 and 10 by interconnecting vapour pipe 50. Used stripping agent together with a content of alcohol is removed from the column through outlet 8 at the top of the column.

In the reaction column, the feed-solution is passed via the drain-plates mounted on every tray and reaction volume from a stripping tray to a succeeding reaction volume.

In the embodiment shown in the FIGURE, the feed stream is adjusted to a temperature requested for the thermal decomposition of the carbamate, by the hot vapours of the stripping agent, which is passed at an appropriate temperature through the column and through the solution flowing on the trays.

The alcohol formed during thermal treatment of the solution in the reaction volumes is separated when the treated solution flows on the stripping trays. Thereby, the stripping agent bubbles through the solution, and the lower boiling alcohol is transferred into the vapour phase and removed together with vapours of the stripping agent.

By alternately passing the feed-solution through the reaction volumes and over the stripping trays, the content of desired isocyanate increases in the solvent and a product-stream being rich in isocyanate is finally withdrawn from the bottom of the column through outlet 6.

I claim:

1. In a process for the preparation of organic isocyanates having the general formula:

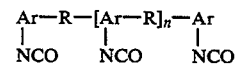

where
- Ar is a optionally substituted phenylgroup;
- R is a methylene or an ethylene group; and
- n is a whole number of from 0 and 2, by thermal decomposition of corresponding carbamates in the presence of an inert solvent, the improvement of which comprises in multiple and separate steps thermally treating the carbamate dissolved in the solvent and, thereby, decomposing the carbamate to isocyanate and an alcohol;

in intermediate steps between the steps of thermal treatment removing the alcohol formed during the thermal treatment by stripping the solvent with an inert stripping agent; and finally recovering a solution being rich in the isocyanate.

2. The process of claim 1, wherein the inert solvent is selected from the group comprising aliphatic hydrocarbons with a carbon number of between 8 and 16, and alkylated and/or halogenated aromatic compounds.

3. The process of claim 2, wherein the solvent comprises decaline, o-diethylbenzene, o-dichlorobenzene, dodecane, hexadecane and biphenyl.

4. The process according to claim 3, wherein the thermal treatment and stripping of the solution are carried out in a reaction column being provided alternatingly with reaction volumes adapted to receive and thermal decompose the carbamate in the solution, and stripping trays adapted to receive the thermal treated solution and stripping off the alcohol from the solution by action of the inert stripping agent being passed through the tray and the solution.

5. The process of claim 2, wherein the solvent is o-dichlorobenzene.

6. The process of claim 5, wherein the solvent is further used as stripping agent.

7. The process according to claim 6, wherein the thermal treatment and stripping of the solution are carried out in a reaction column being provided alternatingly with reaction volumes adapted to receive and thermal decompose the carbamate in the solution, and stripping trays adapted to receive the thermal treated solution and stripping off the alcohol from the solution by action of the inert stripping agent being passed through the tray and the solution.

8. The process according to claim 5, wherein the thermal treatment and stripping of the solution are carried out in a reaction column being provided alternatingly with reaction volumes adapted to receive and thermal decompose the carbamate in the solution, and stripping trays adapted to receive the thermal treated solution and stripping off the alcohol from the solution by action of the inert stripping agent being passed through the tray and the solution.

9. The process according to claim 2, wherein the thermal treatment and stripping of the solution are carried out in a reaction column being provided alternatingly with reaction volumes adapted to receive and thermal decompose the carbamate in the solution, and stripping trays adapted to receive the thermal treated solution and stripping off the alcohol from the solution by action of the inert stripping agent being passed through the tray and the solution.

10. The process according to claim 1, wherein the thermal treatment and stripping of the solution are carried out in a reaction column being provided alternatingly with reaction volumes adapted to receive and thermal decompose the carbamate in the solution, and stripping trays adapted to receive the thermal treated solution and stripping off the alcohol from the solution by action of the inert stripping agent being passed through the tray and the solution.

* * * * *